(12) United States Patent
Dahlberg (10) Patent No.: US 6,951,616 B2
(45) Date of Patent: Oct. 4, 2005

(54) METHOD FOR TREATING A MEDIUM WITH ULTRASONIC TRANSDUCERS

(75) Inventor: Hakan Dahlberg, Uppsala (SE)

(73) Assignee: Ultra Technology Europe AB (SE)

( * ) Notice: Subject to any disclaimer, the term of this patent is extended or adjusted under 35 U.S.C. 154(b) by 128 days.

(21) Appl. No.: 10/643,828

(22) Filed: Aug. 19, 2003

(65) Prior Publication Data

US 2004/0154994 A1 Aug. 12, 2004

Related U.S. Application Data

(63) Continuation-in-part of application No. 10/451,962, filed as application No. PCT/SE02/02195 on Nov. 28, 2002.
(60) Provisional application No. 60/339,380, filed on Dec. 11, 2001.

(51) Int. Cl.$^7$ ................................................. C02F 1/48
(52) U.S. Cl. ...................................... 210/748; 210/805
(58) Field of Search ................................ 210/748, 160, 210/167, 783, 805

(56) References Cited

U.S. PATENT DOCUMENTS

| | | | | |
|---|---|---|---|---|
| 4,346,011 A | * | 8/1982 | Brownstein | 210/748 |
| 5,858,104 A | * | 1/1999 | Clark | 134/1 |
| 6,016,023 A | * | 1/2000 | Nilsson et al. | 310/341 |
| 6,224,826 B1 | * | 5/2001 | Katakura et al. | 422/20 |
| 6,652,733 B2 | * | 11/2003 | Napper | 205/335 |

* cited by examiner

*Primary Examiner*—Betsey Morrison Hoey
(74) *Attorney, Agent, or Firm*—Rolf Fasth; Fasth Law Offices (57) ABSTRACT

The method is for treating a liquid or a slurry of a liquid and solids, such as sludge, soil or fiber webs, with an ultrasonic energy. Movable endless members (214, 230) are provided that are permeable to the liquid portion of a slurry (204). An ultrasonic transducer (236) is disposed adjacent to the member (214) and the ultrasonic transducer (234) is disposed adjacent to the member (230). The slurry is fed in between the members (214, 230). The transducers (234, 236) generate pressure pulses through the members (230, 214) to form imploding bubbles (227) in the slurry. The bubbles (227) have a diameter (d5) that is greater than a distance (d3) between the transducer (234) and the member (230) and a distance (d4) between the transducer (236) and the member (214) to prevent the bubbles (227) from being captured between the transducers (234, 236) and the members (230, 214). In this way, the imploding bubbles can generate intense pressure, temperature and flow speed pulses in the slurry which can create sonochemical or sonophysical changes of the substances in the slurry without harming the ultrasonic transducer surfaces.

10 Claims, 12 Drawing Sheets

METHOD FOR TREATING A MEDIUM WITH ULTRASONIC TRANSDUCERS

PRIOR APPLICATION

This is a continuation-in-part application of U.S. patent application Ser. No. 10/451,962, still pending filed 27 Jun. 2003 that claims priority from PCT application no. PCT/SE02/02195, filed 28 Nov. 2002, that claims priority from U.S. provisional patent application Ser. No. 60/339,380, filed 11 Dec. 2001.

TECHNICAL FIELD

The present invention is a method for treating slurry or a liquid, such as sludge or polluted water in sewage works, with ultrasonic transducers.

BACKGROUND AND SUMMARY OF INVENTION

Ultrasonic energy has been applied to liquids in the past. Sufficiently intense ultrasonic energy applied to a liquid, such as water, produces cavitation that can induce changes in the physiochemical characteristics of the liquid. The subject of sonochemistry, which deals with phenomena of that sort, has grown very much during recent years.

The published material in sonochemistry and related subjects all pertains to batch processes, that is, the liquid solution or dispersion to be treated is placed in a container. The liquid in the container is then stirred or otherwise agitated, and ultrasound is applied thereto. It is then necessary to wait until the desired result, physical or chemical change in the liquid, is achieved, or until no improvement in the yield is observed. Then the ultrasound is turned off and the liquid extracted. In this way liquid does not return to its initial state prior to the treatment with ultrasonic energy. In this respect, the ultrasound treatment is regarded as irreversible or only very slowly reversible.

Far from all industrial processes using liquids are appropriately carried out in batches, as described above. In fact, almost all large-scale processes are based upon continuous processing. The reasons for treating liquids in continuous processes are many. For example, the fact that a given process may not be irreversible, or only slowly reversible, and requires that the liquid be immediately treated further before it can revert to its previous state.

Shock waves external to collapsing bubbles driven onto violent oscillation by ultrasound are necessary for most if not all physiochemical work in liquid solutions. The underpressure pulses form the bubbles and the pressure pulses compress the bubbles and consequently reduce the bubble diameter. After sufficient number of cycles, the bubble diameter is increased up to the point where the bubble has reached its critical diameter whereupon the bubble is driven to a violent oscillation and collapses whereby a pressure and temperature pulse is generated. A very strong ultrasound field is forming more bubbles, and drives them into violent oscillation and collapse much quicker.

A bubble that is generated within a liquid in motion occupies a volume within said liquid, and will follow the speed of flow within said liquid. The weaker ultrasound field it is exposed to, the more pulses it will have to be exposed to in order to come to a violent implosion. This means that the greater the speed of flow is, the stronger the ultrasound field will have to be in order to bring the bubbles to violent implosion and collapse. Otherwise, the bubbles will leave the ultrasound field before they are brought to implosion. A strong ultrasound field requires the field to be generated by very powerful ultrasound transducers, and that the energy these transducers generate is transmitted into the liquid to be treated. Based upon this requirement, Bo Nilsson and Håkan Dahlberg started a development of new types of piezoelectric transducer that could be driven at voltages up to 13 kV, and therefore capable of generating very strong ultrasonic fields.

A very strong ultrasonic source will cause a cushion of bubbles near the emitting surface. The ultrasound cannot penetrate through this cushion, and consequently no ultrasound can penetrate into the medium to be treated. The traditional way to overcome this problem is to reduce the power in terms of watts per unit area of emitting surface applied to the ultrasonic transducers. As indicated above, the flow speed of the medium to be treated will require a stronger ultrasound field and therefore an increased power applied to the ultrasonic transducers. The higher the power input is, the quicker the cushion is formed, and the thicker the formed cushion will be. A thick cushion will completely stop all ultrasound penetration into a liquid located on the other side of this cushion. All the cavitation bubbles in this cushion will then stay in the cushion and cause severe cavitation damage to the ultrasound transducer assembly area leading to a necessary exchange of that part of the ultrasound system. This means that little or no useful ultrasound effect is achieved within the substrate to be treated, and that the ultrasound equipment may be severely damaged.

The above-outlined cushion problems also apply to treating bacteria clusters in sludge slurries and treating drainage water from sludge slurries in sewage works that are subjected to ultrasonic treatment. The problems also apply to other processes with ultrasonic treatment of slurries, such as the forming of paper webs, de-inking of recycled pulp and cleaning of polluted soil. They also apply to other processes where liquids are treated with ultrasound, such as treatment of water polluted with solvents, and cleaning of drinking water and sonochemical processes.

One problem with the currently used sludge ultrasonic treatment plants is that the energy consumption is high and the efficiency could be improved. There is a need to solve the problems outline above so that sewage works may use ultrasonic treatment for bacteria in the sludge without encountering the undesirable cushion effect or the low efficiency. The method of treating a sludge slurry of the present invention provides a solution to the problems outlined above.

More particularly, the method of the present invention is for treating a slurry, such as sludge, with an ultrasonic energy without creating the undesirable cushion effect. Movable endless members are provided that are permeable to the liquid part of a sludge slurry and a first ultrasonic transducer is disposed adjacent to a first movable member and a second ultrasonic transducer is disposed adjacent to a second movable member. The slurry is fed in between the two movable members. The transducers generate pressure pulses through the members to form imploding cavitation bubbles in the sludge slurry that have an effect on the bacteria clusters. The cavitation bubbles have a resonance diameter ($d_5$) at the ultrasound frequency used that is greater than a distance ($d_3$) between the first transducer and the first member and a distance ($d_4$) between the second transducer and the second member to prevent the bubbles from imploding between the transducers and the members. By making the distance between the members smaller and smaller along the ultrasonic treatment path, a hydraulic pressure build-up between the members causes a dewatering of the slurry through the members giving a higher and higher dry solids content of the sludge slurry that is favorable for the efficiency of the ultrasonic treatment. The edges of the upper and lower members are pressed together to prevent the sludge from leaving the treatment zone in the cross machine direction. When treating liquids there are wedge formed sidewalls between the members and the edges of the members are pressed towards these sidewalls and the contact areas are water lubricated to minimize friction. The treated sludge may then be pumped to an anaerobic fermentation tank. Biogas can be continuously removed from the sludge by the under-pressure in a degassing pump or other degassing unit in a circulation loop connected to the fermentation tank before any gas bubbles are formed in the fermentation tank. The sludge slurry may again be subject to degassing and ultrasonic treatment before the slurry is sent to a press unit for dewatering.

DETAILED DESCRIPTION

Figure 1:
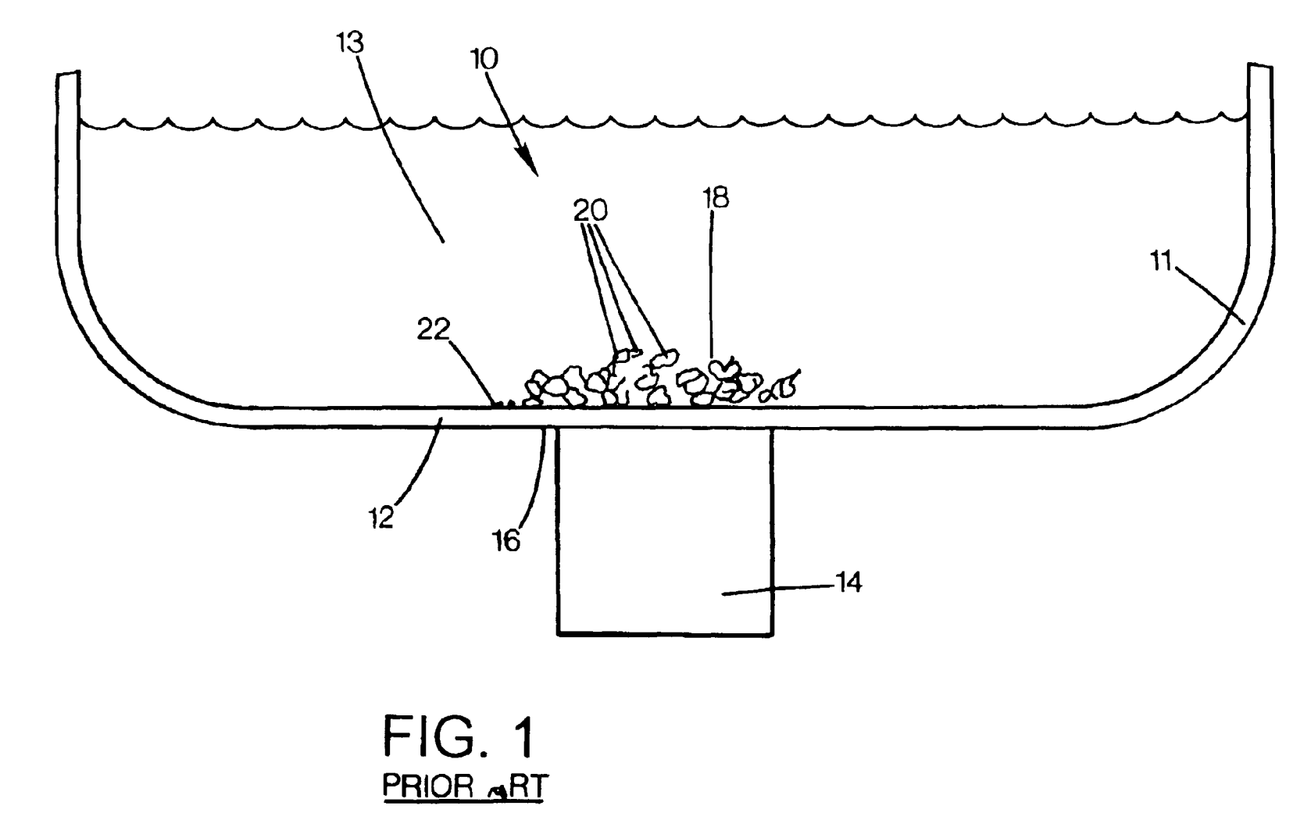
FIG. 1 is a schematic side view of the formation of a reactor of a prior art system.

FIG. 1 is a side view of a prior art transducer system 10 that has a container 11, such as a stainless reactor, with a wall 12 for containing a liquid 13. A transducer 14 is attached to an outside 16 of the wall 12. When the transducer 14 is activated, a pillow 18 of cavitation bubbles 20 are formed on an inside 22 of the wall 12 due to the fracture zone in the liquid 13 that may be a result of fracture impressions on the inside 22 of the wall 12. The bubbles may be held to the inside wall due to the surface tension of the liquid 13. The bubbles 20 are good insulators and prevent the effective transmission of the ultrasonic energy into the liquid 13. The under-pressure pulses of the ultrasonic energy transmitted by the transducer 14 create the cavitation bubbles. In this way, the pressure inside the bubbles is very low.

Figure 2:
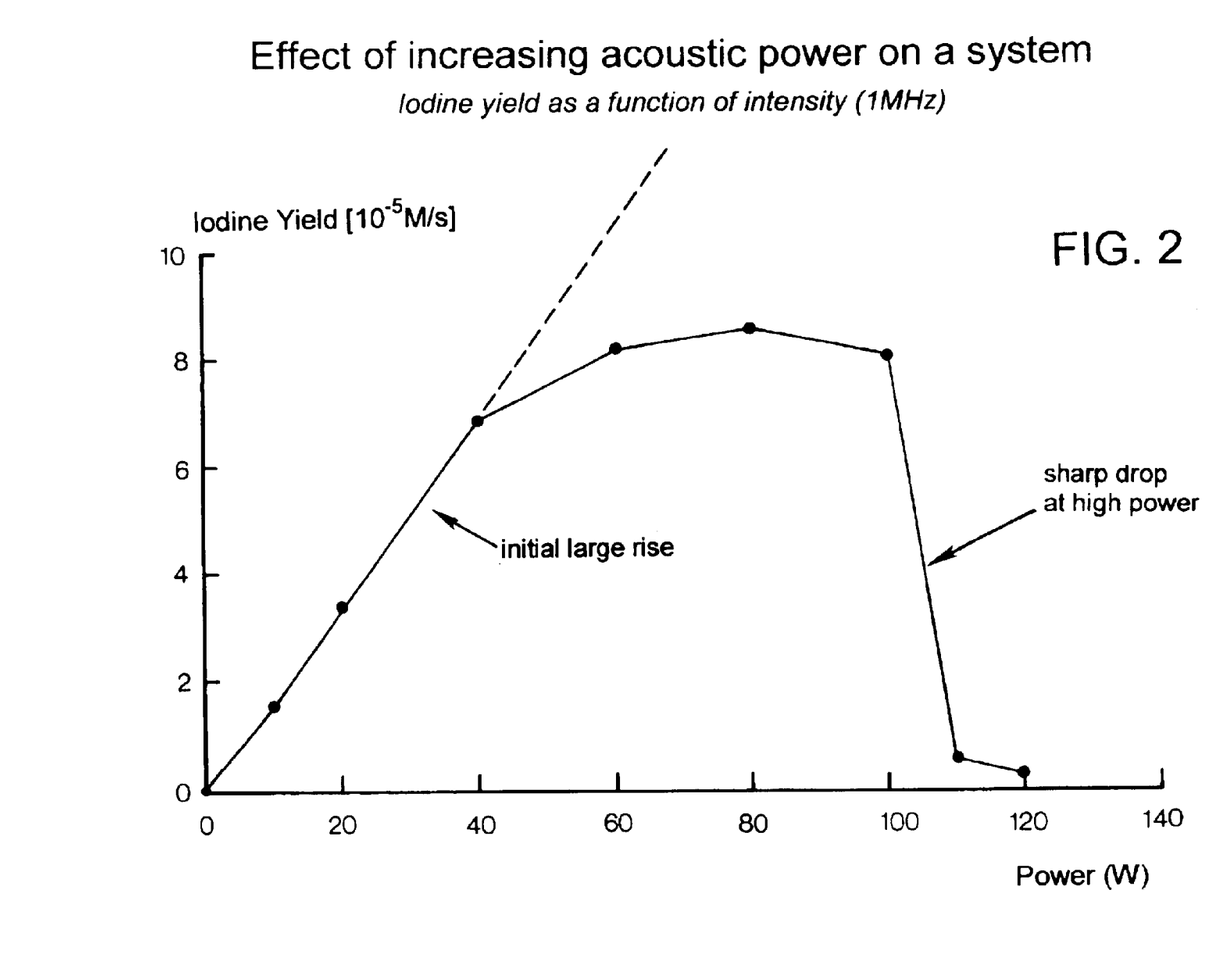
FIG. 2 is a graphical illustration of the correlation between iodine yield and acoustic power.

FIG. 2 is a graphical illustration that shows the iodine yield is affected by increased acoustic power on the system 10. The more power is applied, the thicker the formation of the bubbles 20, as shown in FIG. 1, and the yield increase is reduced and drops sharply at power ratings over 100 Watts in this case. In this way, the cavitation bubbles severely limit the usefulness of increasing the acoustic power to improve the iodine yield.

Figure 3:
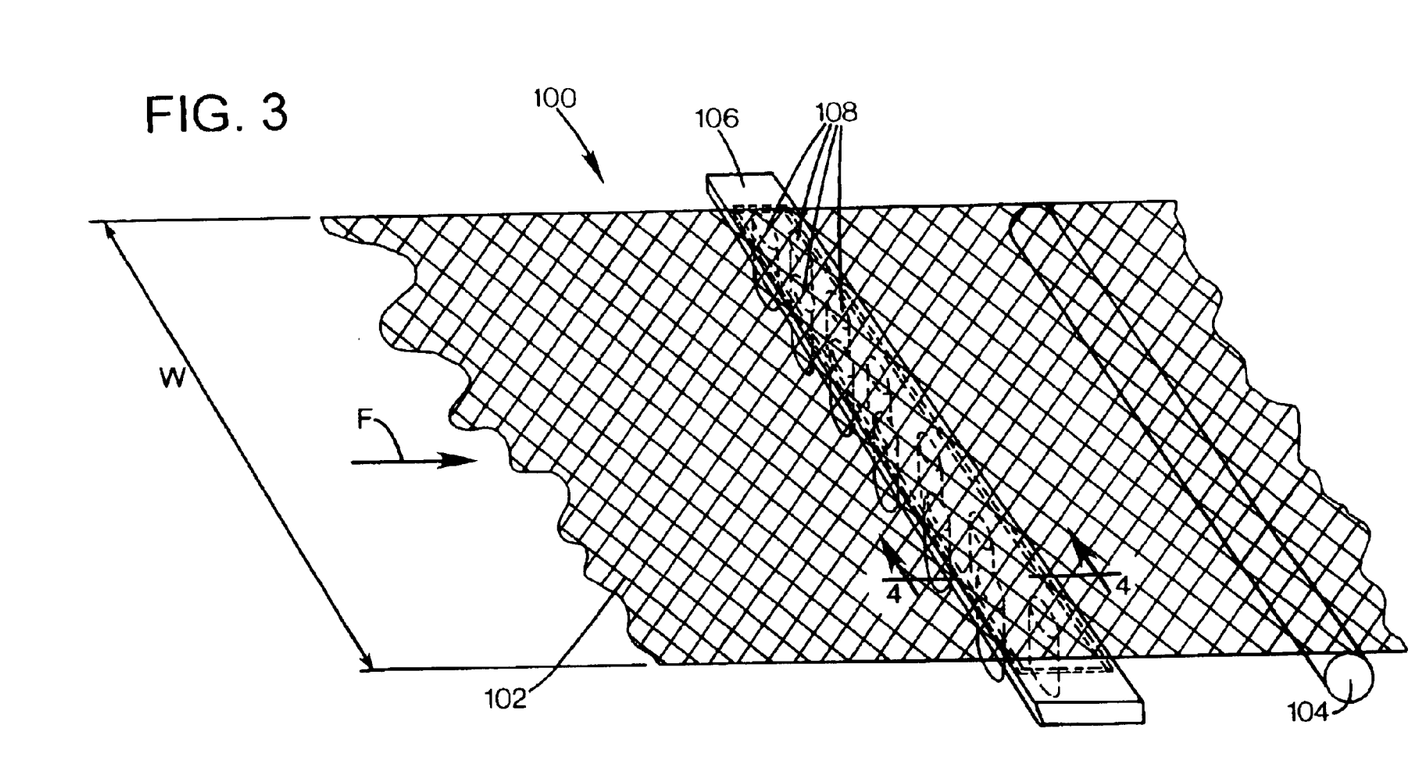
FIG. 3 is a perspective view of the transducer system of the present invention disposed below a movable endless member.

FIG. 3 is a perspective view of the transducer system 100 of the present invention. The system has a movable endless permeable medium 102, such as a woven material, paper machine plastic wire or any other bendable medium permeable to liquids, that is rotatable about rollers 104 that guide the medium 102 in an endless path. As explained below, it is important that the medium is permeable to a liquid that may carry ultrasonic energy to the liquid disposed above the medium 102 so as to effectively create the cavitation bubbles in the liquid or slurry to be treated. The ultrasonic energy may be used to reduce flocculation 163, best shown in FIG. 5A, of fibers in the liquid to be treated because the bubbles implode or collapse to generate pressure pulses to the fiber flocculation 163 so that the fibers are separated from one another to evenly distribute or disperse the fibers in the liquid. The pressure pulses may be about 500 to 1000 bars so the pulses are more forceful than the forces that keep the fiber flocculation together. In general, the longer the fibers are or the higher the fiber consistency is, the higher the tendency of flocculation.

The medium may have a rotational speed up to 2000 meters per minute in a forward direction as shown by an arrow (F). An elongate foil 106, made of, for example, steel or titanium is disposed below the permeable medium 102 and extends across a width (W) of the medium 102. A plurality of transducers 108, such as magnetostrictive, piezoelectric or any other suitable type of transducers, is in operative engagement with the foil 106 such as by being integrated therewith or attached thereto.

Figure 4:
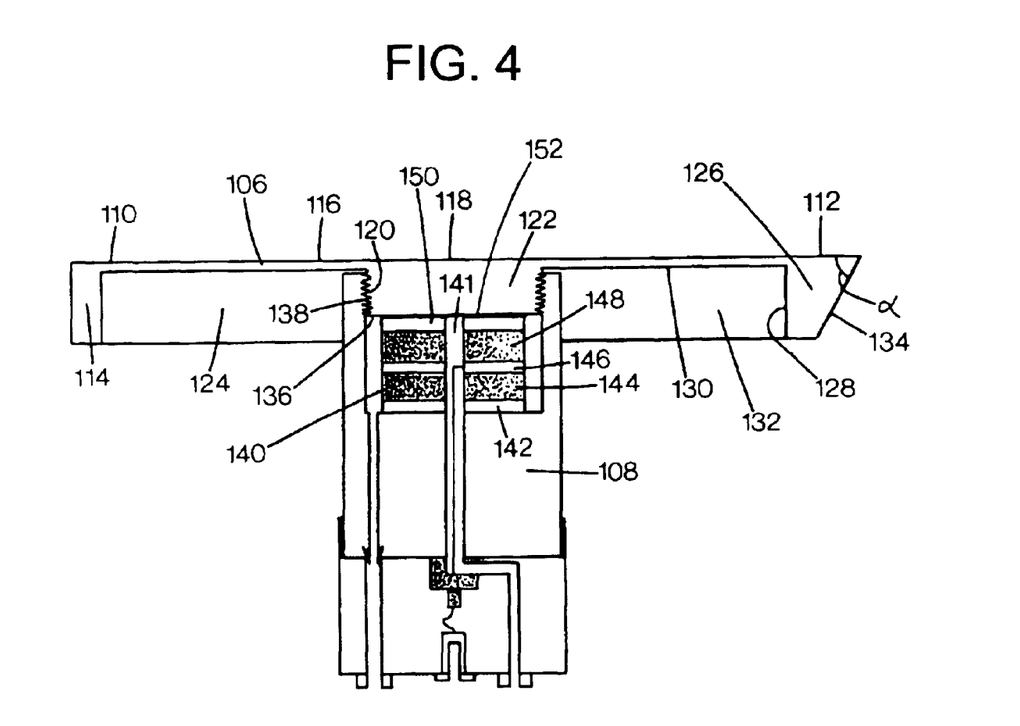
FIG. 4 is a cross-sectional view along line 4—4 in FIG. 3.

FIG. 4 is a detailed view of one of the transducers 108 attached to a mid-portion 118 of the hydrodynamic foil 106. More particularly, the foil 106 has a rear portion 110 and a front portion 112. The rear portion 110 has a rectangular extension 114 that extends away from a top surface 116 of the foil 106. The mid-portion 118 of the foil 106 has a threaded outside 120 of a connecting member 122 also extending away from the top surface 116 so that a cavity 124 is formed between the extension 114 and the connecting member 122.

The front portion 112 has an extension 126 that extends away from the top surface 116 and has a back wall 128 that is perpendicular to a bottom surface 130 of the foil 106 so that a cavity 132 is formed between the back wall 128 and the member 122. The extension 126 has a front wall 134 that forms an acute angle alpha with the top surface 116. The cavities 124 and 132 provide resonance to the ultrasound transmitted by the transducers 108 to reinforce the amplitude of the vibrations of the ultrasound. The front wall 134 forms an acute angle alpha with a top surface 116 of the foil 106 to minimize the pressure pulse when the water layer under the member is split by the front wall 134 so a larger part of the water is going down and only a minor part is going between the top side of the foil 116 and the member 102. When the member 102 is moving over the foil surface 116 a speed dependant under-pressure is created that will force down the member 102 against the foil surface 116. When the member is leaving the foil 106 there is room to urge the liquid 156 through the member 102.

In other words, the design of the extension 126 is particularly suitable for paper manufacturing that has slurry of water and fibers. The water layer split at the front wall 134 creates an under-pressure pulse so that the water on top of the moving member flows through the member 102 and into a container there below. The design of the extension 126 may also be designed for other applications than paper making that is only used as an illustrative example.

The transducer 108 has a top cavity 136 with a threaded inside wall 138 for threadedly receiving the member 122. The transducer 108 may be attached to the foil 106 in other ways. For example, adhesion or mechanical fasteners may attach the transducer. The present invention is not limited to the threaded connection described above.

Below the top cavity 136, a second housing cavity 140 is defined therein. The cavity 140 has a central segment 141 to hold a bottom cooling spacer 142, a lower piezoelectric element 144, a middle cooling spacer 146, an upper piezoelectric element 148 and a top cooling spacer 150 that bears against a bottom surface 152 of the connecting member 122. The spacers 142, 146, 150 are used to lead away the frictional heat that is created by the elements 144, 148.

By using three spacers, all the surfaces of the elements 144, 148 may be cooled. As the piezoelectric elements 144, 148 are activated, the thickness of the elements is changed in a pulsating manner and ultrasonic energy is transmitted to the member 122. For example, by using a power unit with alternating voltage of a level and frequency selected to suit the application at hand, the elements 144, 148 start to vibrate axially. In this way, if the AC frequency is 20 kHz then a sound at the same frequency of 20 kHz is transmitted. It is to be understood that any suitable transducer may be used to generate the ultrasonic energy and the invention is not limited to piezoelectric transducers.

Figure 5:
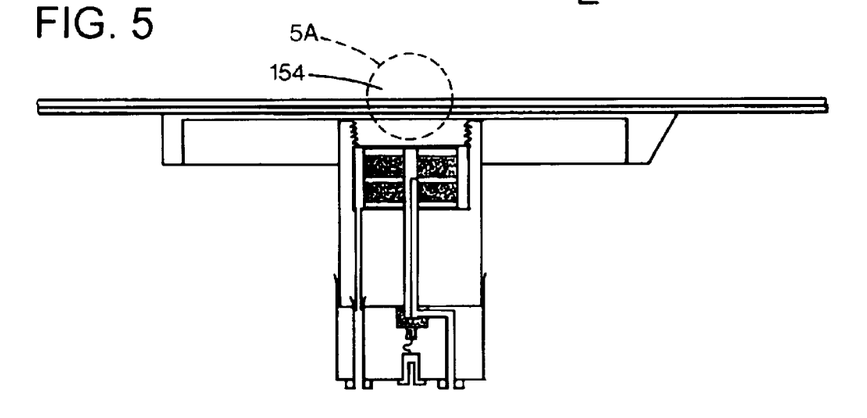
FIG. 5 is an enlarged view of cavitation bubbles dispersed in slurry disposed above the movable endless medium.
Figures 5A, 5B:
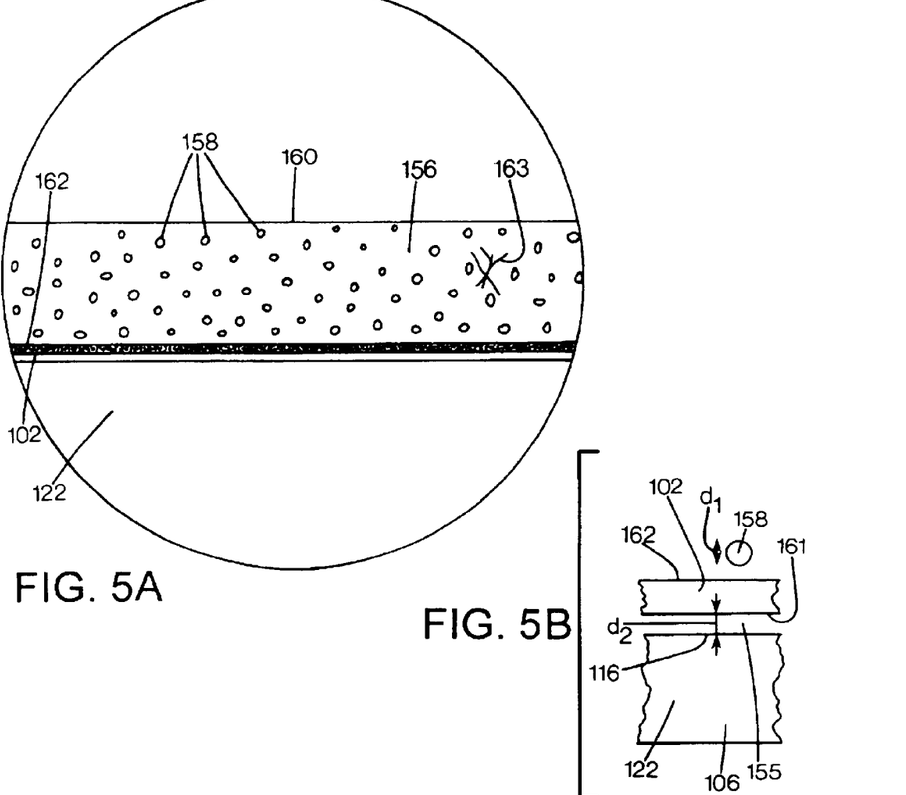

FIG. 5 is an enlarged view of a central segment 154 so that the permeable movable member 102 bears or is pressed against the top surface 116 of the member 122 of the foil 106 so there is not sufficient space therebetween to capture cavitation bubbles. In other words, an important feature of the present invention is that a gap 155 defined between the foil 106 and the member 102 is much less than the critical bubble diameter so that no bubbles of critical size can be captured therebetween. The gap 155 between the member 102 and the foil 106 is defined by the tension in the member 102, the in-going angle between the member 102 and the foil 106, the pressure pulse induced by the water layer split at the front of the foil 106, the geometry of the foil 106, the under-pressure pulse when the member 102 leave the foil 106 and the out-going angle of the member 102. The bubbles 158 have a diameter d1 that is much longer than the distance d2 of the gap 155 between the top surface 116 of the foil 106 and the bottom surface 161 of the permeable member 102. In this way and by the fact that the member 102 is moving, the cavitation bubbles 158 are forced to be created above the permeable member 102 and by imploding disperse the liquid substance 156 that is subject to the ultrasonic treatment and disposed above the member 102. The liquid substance 156 has a top surface 160 so that the bubbles 158 are free to move between the top surface 160 of the substance 156 and a top surface 162 of the member 102. In general, the effect of the ultrasonic energy is reduced by the square of the distance because the liquid absorbs the energy. In this way, there are likely to be more cavitation bubbles formed close to the member 102 compared to the amount of bubbles formed at the surface 160. An important feature is that because the member 102 is moving and there is not enough room between the foil 106 and the member 102, no cavitation bubbles are captured therebetween or along the top surface 162 of the movable member 102.

Figure 6:
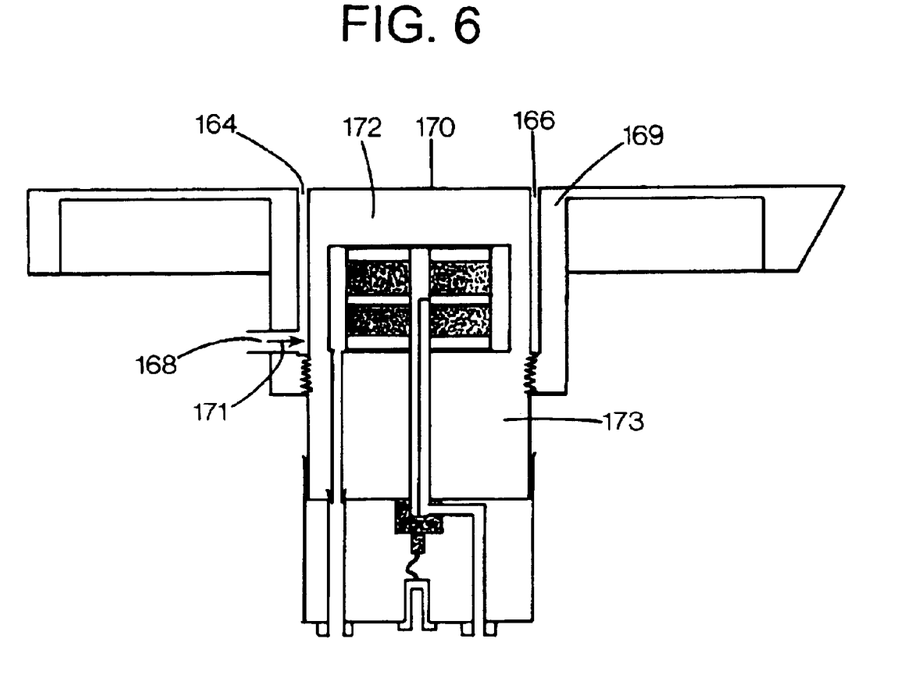
FIG. 6 is a cross-sectional view of a second embodiment of the transducer system of the present invention.

The second embodiment of a transducer system 173 shown in FIG. 6 is virtually identical to the embodiment shown in FIG. 4 except that the transducer system 173 has a first channel 164 and a second channel 166 defined therein that are in fluid communication with an inlet 168 defined in a foil member 169. The channels 164, 166 extend perpendicularly to a top surface 170 of a connecting member 172. The channels 164, 166 may extend along the foil 169 and may be used to inject water, containing chemicals, therethrough. For example, in papermaking, the chemicals may be bleaching or softening agents. Other substances such as foaming agents, surfactant or any other substance may be used depending upon the application at hand. The ultrasonic energy may be used to provide a high pressure and temperature that may be required to create a chemical reaction between the chemicals added and the medium. The channels 164, 166 may also be used to add regular water, when the slurry above the moving member is too dry, so as to improve the transmission of the ultrasonic energy into the slurry. The chemicals or other liquids mentioned above may also be added via channels in the front part of the transducer assembly bar 106. If the liquid content of the medium to be treated is very low, the liquid may simply be applied by means of spray nozzles under the web. Also in those cases may the applied liquid be forced into the web by the ultrasonic energy and afterwards be exposed to sufficient ultrasound energy to cause the desired reaction to take place between the chemicals and the medium to be treated.

Figure 7:
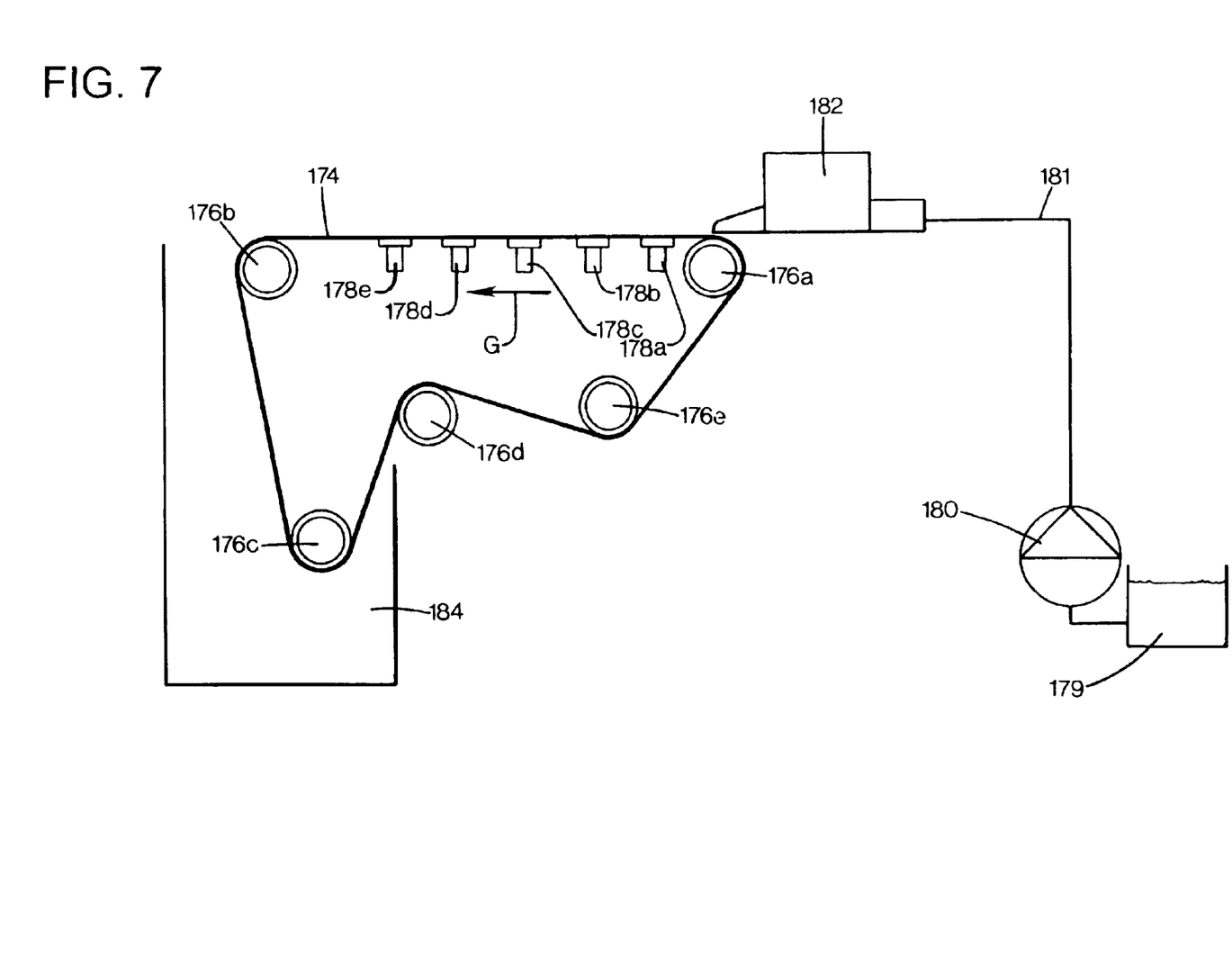
FIG. 7 is a cross-sectional view of a plurality of transducers disposed below a movable endless medium.

FIG. 7 is an overall side view showing an endless bendable permeable member 174 that is supported by rollers 176a–e. Below the member 174 is a plurality of transducer systems 178a–e for increased output by adding more ultrasonic energy to the system. By using a plurality of transducers, different chemicals may be added to the slurry 179, as required. The slurry 179 contains fibers or other solids, to be treated with ultrasonic energy, is pumped by a pump 180 in a conduit 181 via a distributor 182 onto the member 174 that moves along an arrow (G). The treated fibers may fall into a container 184.

The transducer system of the present invention is very flexible because there is no formation of cavitation bubble pillows in the path of the ultrasonic energy. By using a plurality of transducers, it is possible to substantially increase the ultrasonic energy without running into the problem of excessive cavitation bubbles to block the ultrasound transmission. The plurality of transducers also makes it possible to add chemicals to the reactor in different places along the moving member, as required.

Figure 8:
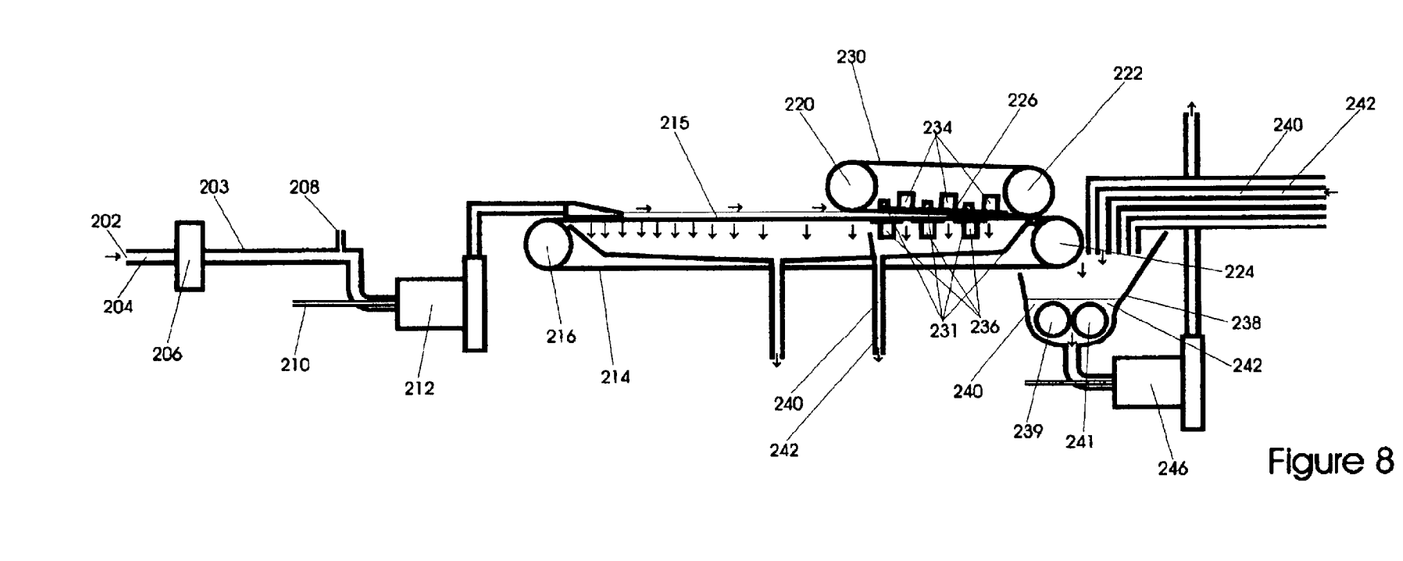
FIG. 8 is a schematic view of a portion of a sludge plant of the present invention.

FIG. 8 shows a portion of a sludge treatment plant 200 that has a sludge inlet 202 of a pipe 203 so that a slurry such as a sludge 204 may be pumped through a fiberizer device 206 for dispersing lumps and other aggregates that may have been formed in the sludge 204. The plant 200 may be a full flow system that permits the continuous feeding in with ultrasonic treatment, continuous circulation with ultrasonic treatment and continuous feeding out with ultrasonic treatment of the sludge slurry 204, but in that case three separate ultrasound treatment units are needed. The shown plant 200 is meant for part time input with ultrasonic treatment, full time circulation, part time circulation with ultrasonic treatment and part time output to press with ultrasonic treatment Biological drainage and retention aid tube 208 may be in fluid communication with the pipe 203 to permit the addition of biological drainage substances and other treatment substances into the pipe 203. The sludge 204 flows into a specialized pump 212 that not only functions as a regular pump but also deaerates the sludge before pumping the sludge onto an endless member such as a continuous movable under-wire 214 that may be similar to the endless member 102, described above. The deaeration is used to improve drainage of the sludge on the wire 214 and to reduce the required length of the ultrasound treatment. The centrifugal pump 212 may have a centrifuge drum connected to the pump wheel and an outlet 210 at the center of the pump inlet to allow low-density substances, such as air and other gases, to be separated from the sludge 204 that exits the pump along the outward periphery of the pump 212. The use of the fiberizer device 206 and the pump 212 provide for improved dewatering and higher effectiveness of the ultrasound treatment.

When the sludge enters the rotatable under-wire 214, the sludge is further dewatered by gravitation in a pre-drain zone 215 so that the dry substance content of the sludge 204 is increased to about 5–8%. The wire 214 extends and is supported by the rollers 216, 224 so that an endless loop is formed.

The plant system 200 also has an upper wire 230 that extends between and is supported by the rollers 220, 222. The upper wire 230 exerts some pressure on the sludge disposed on the under wire 214. The rollers 222 and 224 form a nip 226. A plurality of vacuum or suction units 231 is disposed above the upper wire 230. In this way, the sludge is subjected to both an upwardly directed, via vacuum and hydraulic pressure, and downwardly directed, via gravitation and hydraulic pressure, dewatering processes so that the dry substance content of the sludge is increased from about 5–8% at the roller 220 to about 10–15% after the nip 226. A vacuum or suction unit 231 is disposed under the lower wire 214 to bring the sludge cake to follow the lower wire 214 when the wires separate after the nip 226. Ultrasonic transducers 234 are disposed above the upper wire 230 and ultrasonic transducers 236 are disposed below the under-wire 214 so that the sludge is continuously subjected to ultrasound treatment, similar to the ultrasound treatment described in detail above, between the rollers 220, 222. As a result of the dewatering process, the average dry substance content of the sludge is about 8–11% during the ultrasonic treatment in the nip 226. The very high dry substance content reduces the specific energy consumption to about half of conventional systems.

After the first ultrasound treatment, most of the bacteria cell walls are punctured and those bacteria are killed. In this way, the inside bacteria protoplasm is dispersed into the sludge/water suspension so that anaerobic bacteria in the fermentation tank can attack and chemically degrade the exposed bacteria, bacteria walls and protoplasm much faster, as described in detail below.

Figure 9:
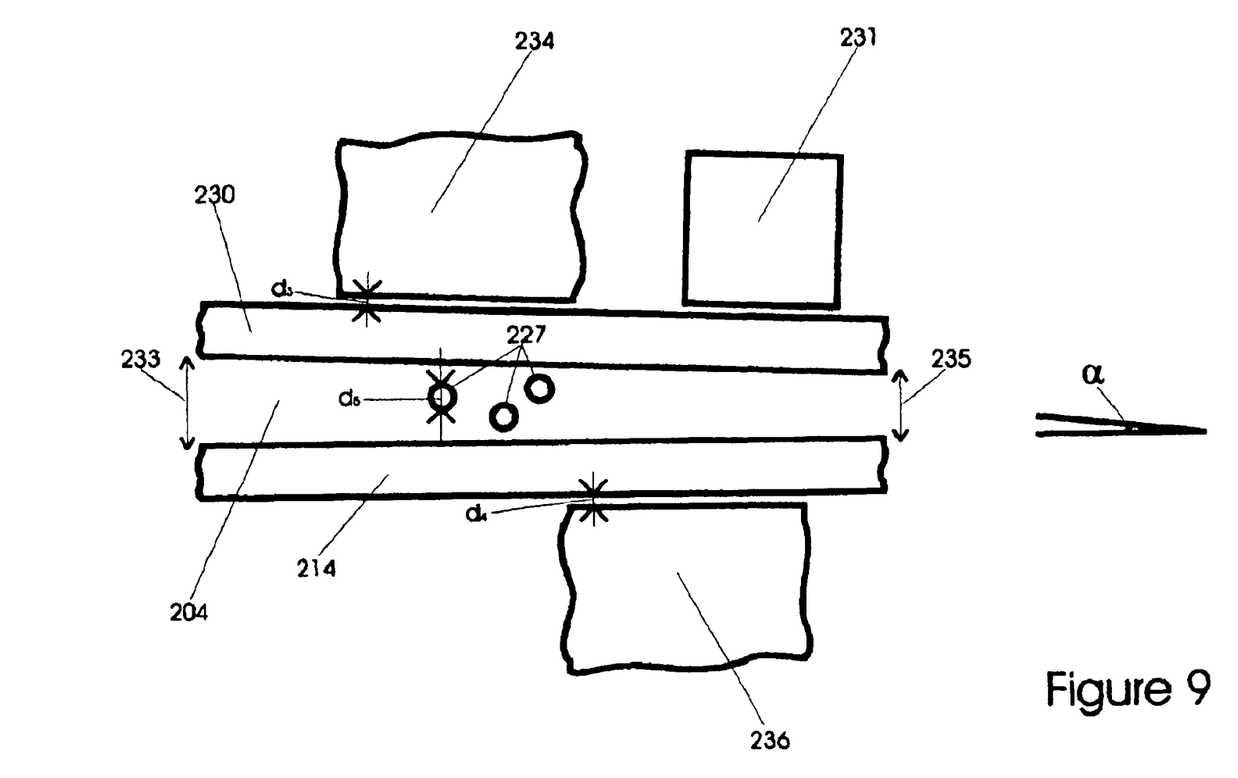
FIG. 9 is a detailed view of the wires and ultrasonic transducers of the device of the present invention.

As best shown in FIG. 9, the transducers 234, 236 are placed so close to the wires 214, 230 so that the distance (d3) between the transducers 234 and the wire 230 is significant less than a diameter (d5) of a cavitation bubble 227 of critical size at used ultrasonic frequency. Similarly, the distance (d4) between the transducers 236 and the under-wire 214 is less than the diameter (d5) so that no cavitation bubbles 227 of critical size at used ultrasonic frequency may be captured between the transducers and the wires 214, 230. The wire 214 may be slightly angled or wedged relative to the upper wire 230 so that a gap 233 at an incoming end is slightly greater than a downstream gap 235. The pressure on the sludge is thus gradually increased between the rotatable wires 214, 230 as the sludge dryness increases. The wires 214, 230 may also be parallel, if desired.

The sludge that has been treated with the ultrasound then falls from the wire 214 into a mixer 238 that tears substances into pieces with the spiral formed fins on the cylinders 239, 241. The mixer 238 mixes the treated sludge 204 with water 240 that comes from the ultrasound portion of the wire 214. This water 240 includes all the enzymes and other biologically degradable substances 242 that may be in liquid form drained from the punctured bacteria in the sludge slurry. The sludge is then deaerated in a specialized pump 246.

Figure 10:
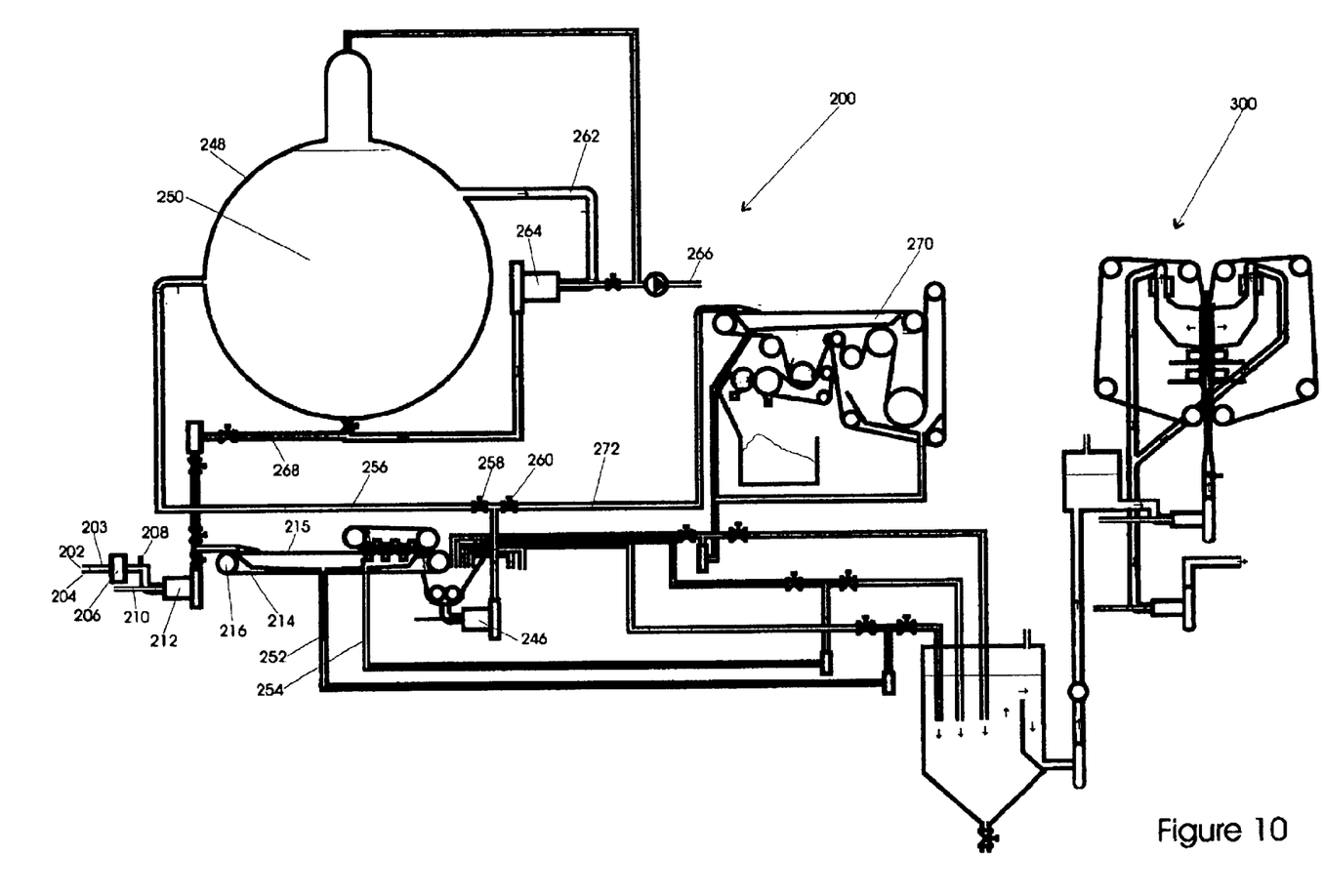
FIG. 10 is a schematic view of the sludge and drainage water treatment plant of the present invention.

FIG. 10 shows a bigger portion of the plant 200 compared to FIG. 8. The drainage water from the pre-drain zone 215 is led into a conduit 252 that may later be fed back into the mixer 238 or into the water treatment section 300 of the plant. A portion of the drainage water that includes the protoplasm from the collapsed bacteria flows through the vacuum or suction devices 231 and pumped direct into the mixer 238. Another portion of the ultrasound treated drainage water flows into a conduit 254 and is led back into the mixer 238. The sludge concentration is now reduced to about 5–6% in view of the added treated drainage water and is forwarded to the pump 246. The pump 246 deaerates the sludge so that air is removed in view of the anaerobic environment and reactions in the fermentation tank 248. The pump 246 then pumps the treated sludge including the treated drainage water, via a conduit 256, to the fermentation tank 248. The conduit 256 may have valves 258, 260. The tank 248 is filled with sludge 250 that has a dry substance content of about 5–6% that is the about the same as the sludge dry substance content in the mixer 238 that, in turn, is about the same as the sludge dry substance content prior to the ultrasonic treatment at the roller 220. It may also be possible to add retention/drainage chemicals and fibers directly into the mixers 238. This is done only when the sludge is destined to the dewatering press. No or very little gas should remain at the top of the tank 248 since the pump 246 removes the gas. Preferably, some gas should remain at the top of the tank 248 and the tank may be equipped with two safety valves in case of power outages. The biogas that is produced in the tank 248 has a much higher methane concentration compared to conventional treatment methods. The methane concentration is about 70–75% compared to 58–62% when conventional methods have been used. Also, the amount of biogas produced is higher. The sludge may be circulated in a conduit 262 connected to a third specialized pump 264 that removes biogas from the system. There is methane producing anaerobic bacteria in the sludge slurry 250 in the tank 248. The methane gas is produced inside the cell membrane of the anaerobic bacteria and if the methane concentration is high in the slurry 250, it becomes more difficult for the methane gas to escape through the cell membrane and into the slurry. By removing some of the methane gas in the slurry 250, the osmotic transfer of the methane gas from the inside of the cell membrane out to the slurry is enhanced. If no methane gas is removed from the slurry 250, the osmotic transfer may slow down drastically when the methane gas concentration is so high in the slurry 250 that it goes into saturation and gas bubbles start to grow. It should be noted that it with this invention is not necessary to wait until biogas bubbles are formed and float to the surface of the slurry 250 so that the biogas can be withdrawn from the top of the tank 248 as in conventional systems. The pump 264 returns the sludge back into the tank 248 but with substantially less biogas concentration. The biogas retrieved by the pump 264 may flow into a conduit 266.

The plant 200 may be run in sequences. The first ⅓ of the time the tank 248 may be fed with ultrasonic treated and deaerated sludge according to the system described above. It is possible to subject the sludge to further ultrasound treatment, according to the system described above. For example, valves may be opened to permit the sludge in the tank 248 to flow into a conduit 268 and back on the wire 214 to again be subjected to the ultrasound treatment. This may be done the second ⅓ of the time, the plant 200 is used so that a part of all new bacteria that have been formed in the tank 248 may be punctured. All drain water, including the drain water from the pre-drain zone 215, may be used in the mixer 238 to bring down the dry substance content to about 6% again before it is deaerated and pumped back into the tank 248. The third ⅓ of the time may be used for feeding the treated sludge into a press unit 270 via a conduit 272. The sludge may be ultrasound treated before the sludge is sent to the press unit 270 to make sure as many bacteria cells as possible are punctured since the presses in the press unit can only press out water between the bacteria cells and not fluid that may be disposed inside the cells. In this way, the press efficiency is improved by the ultrasound treatment of the sludge. All the time the plant 200 may at least partly be used for re-circulation in the conduit 262 to remove biogas.

When the fermentation is started in the tank 248, the tank should have a carbon dioxide atmosphere so that the anaerobic bacteria may start working at full capacity on the sludge right away without any competition from aerobic bacteria. For example, the carbon dioxide may be pumped into the tank 248 before any processing has taken place in the tank 248. In this way, any aerobic bacteria in the tank 248 and in the incoming sludge will die due to lack of oxygen and the anaerobic bacteria in the first incoming, at start up not ultrasound treated, sludge may start reproducing without any competition. The ultrasound treatment may be started when a sufficient amount of sludge with live bacteria has been pumped into the fermentation tank 248 with the sludge. The methane producing anaerobic bacteria are used to degrade as big part of the sludge that is pumped into the tank 248 as possible.

It is also possible to serially connect many fermentation tanks so that the gas that is withdrawn by the specialized pump in the circulation conduit from the first tank may be sent forwardly to the circulation of the second tank. The gas that is withdrawn from the second tank may be sent forwardly to the third tank etc. The gas that is withdrawn from the last fermentation tank may be sent away for gas purification. The effectiveness of the methane fermentation is thus further increased so that the methane concentration may reach 80% or higher.

Figure 11:
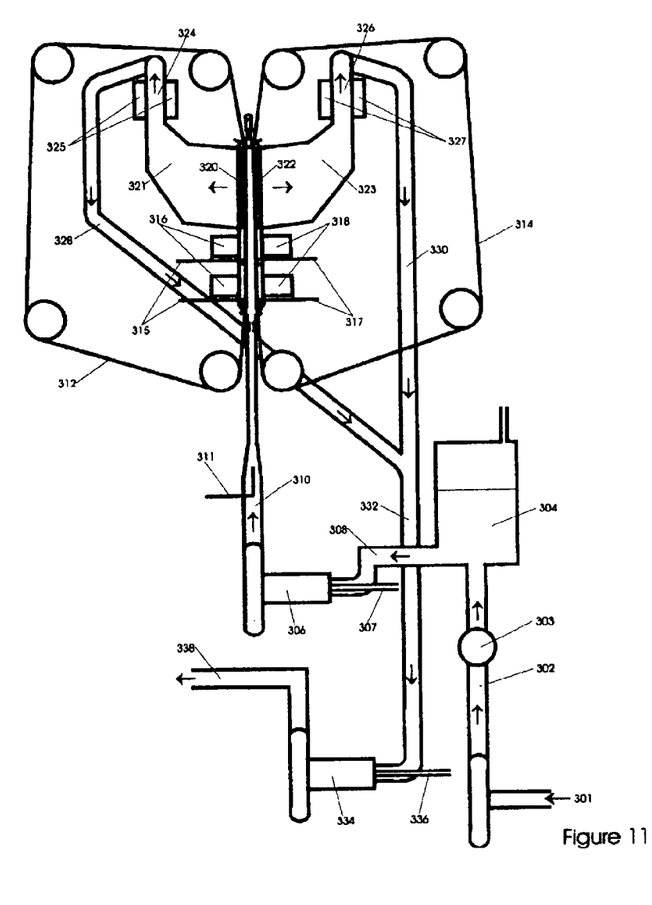
FIG. 11 is a schematic view of the liquid treatment unit of the present invention.

FIG. 11 is a schematic view of the liquid treatment plant 300 of the present invention. A liquid 301, such as water, is conveyed in a conduit 302 that has a pump 305 and passed through a filter 303. The filter 303 removes particles from the liquid that could not pass through the rotatable wires 312, 314. The liquid may then go up into a tank 304 and is then passed through a degassing pump 306 connected to conduits 308 and 310. The tank 304 may be used to regulate the pressure in the pump 306. Gas may be passed through a conduit 307 to that, for example, air or other gas that is dissolved in the liquid is removed from the liquid in the conduit 310. The conduit 310 extends in between two rotatably wires 312, 314 and ozone water may be added at the inlet conduit 311 to kill some of the bacteria and oxidize solvents or other impurities in the liquid. As described in detail above, ultrasound transducers 316 are disposed adjacent to the wire 312 while ultrasound transducers 318 are disposed adjacent to the wire 314. Ozone water may be added into the conduit 310 and also at the transducers 316, 318. The liquid that is passed between the wires 312, 314 is subjected to the ultrasound and the ozone water treatment, 315, 317, respectively, to further reduce the bacteria level in the liquid. There are very good synergy between ultrasonic energy and ozone when dealing with killing rate of bacteria. The treated liquid is then drained at drainage or suction units 320, 322 and into drainage cavities 321, 323. The liquid may be subjected to ultraviolet light 325, 327 at passages 324, 326 to even further reduce the bacteria level. The liquid has to be quite transparent by the time it passes the passages 324, 326 to get good synergy for ultraviolet light together with ultrasonic energy and eventually used ozone according to bacteria killing rate. The liquid may then be conveyed in conduits 328, 330 into a common conduit 332 for degassing treatment in a degassing pump 334 with a gas outlet 336. The treated liquid may be pumped away in a conduit 338. It may be possible to modify the system 300 so that the liquid may be re-circulated several times, as desired.

Figure 12:
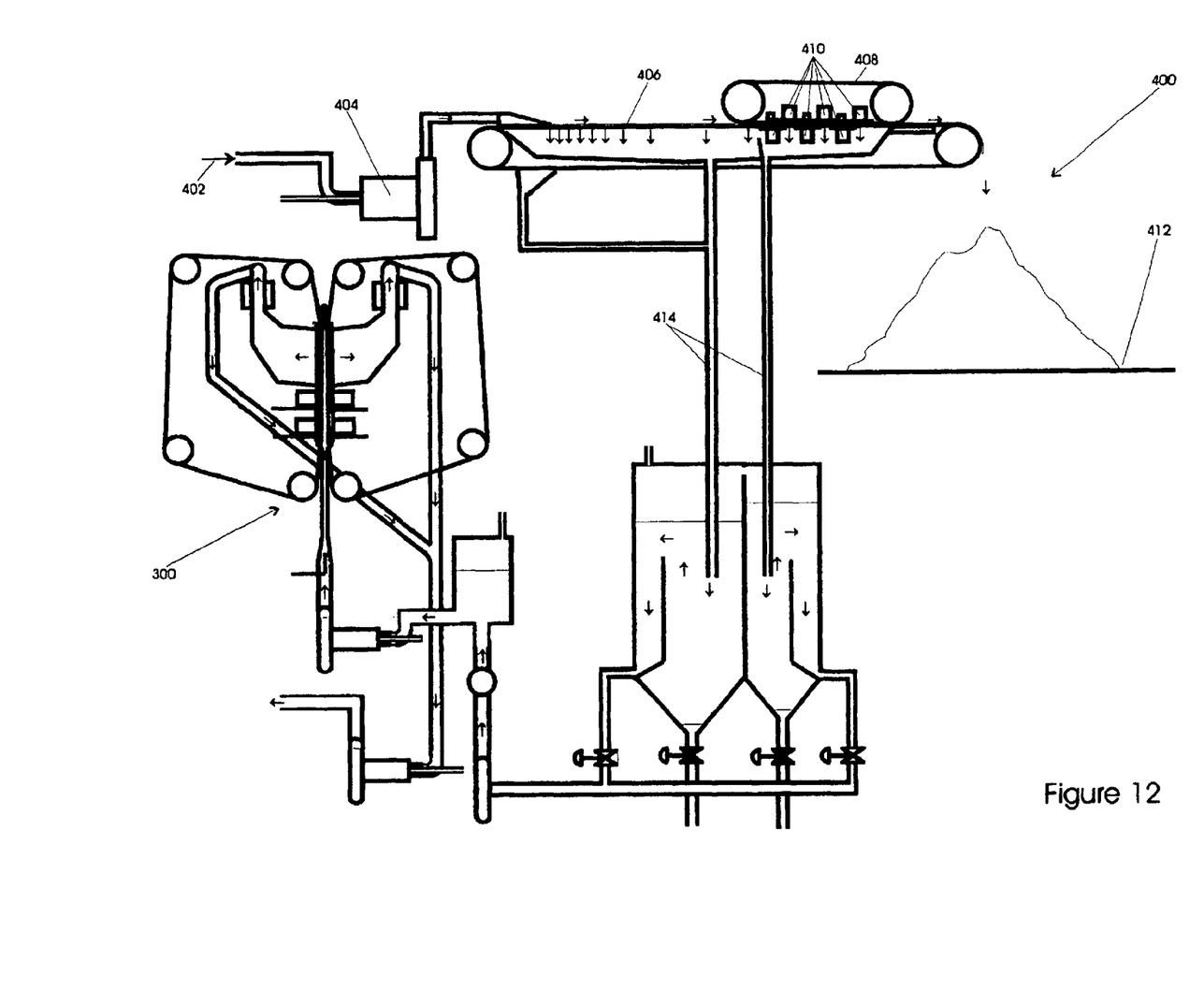
FIG. 12 is a schematic view of another embodiment of the present invention for washing of polluted soil.

FIG. 12 is a schematic illustration of a second embodiment 400 of the present invention for washing of polluted soil in slurry. Polluted soil slurry 402 is conveyed through a pump 404 between movable wires 406, 408. The soil is subjected to ultrasound transducers 410 and the washed soil is collect at a collection site 412. The water 414 that is collected from the soil slurry may be sent to the liquid treatment plant described above. The same ultrasound principles apply as described above.

While the present invention has been described in accordance with preferred compositions and embodiments, it is to be understood that certain substitutions and alterations may be made thereto without departing from the spirit and scope of the following claims.

I claim:

1. A method of treating a liquid or a slurry of a liquid with an ultrasonic energy comprising:

providing a first member being permeable to a medium, and a first vibrating device and the first member having a first gap formed therebetween, the first gap representing a first distance;

providing a second member aligned with the first member and providing a second vibrating device, the second vibrating device and the second member having a second gap formed therebetween, the second gap representing a second distance;

feeding the medium between the first and second members; and the first and second vibrating devices generating pulse through the first and second members, respectively, to form imploding bubbles in the medium disposed between the first and second members, the bubbles having a critical diameter prior to implosion that is greater than the first distance and the second distance to prevent imploding bubbles from being disposed in the first and second gaps.

2. The method according to claim 1 wherein the method further comprises providing a fermentation tank in fluid communication with the first and second members and feeding a slurry to a the fermentation tank.

3. The method according to claim 2 wherein the method further comprises circulating the slurry from the fermentation tank during removal of dissolved biogas in a circulation conduit that is in fluid communication with the fermentation tank.

4. The method according to claim 2 wherein the method further comprises creating an anaerobic environment in the fermentation tank prior to receiving the slurry.

5. The method according to claim 4 wherein the method further comprises collecting protoplasm from collapsed bacteria and other colloidal substances from the slurry.

6. The method according to claim 5 wherein the method further comprises removing air from the slurry from the mixer prior to pumping the slurry to the fermentation tank.

7. The method according to claim 1 wherein the method further comprises gradually narrowing a third gap between the first and second members until a fourth gap is reached between the first and second members and forming an angle (alpha) between the first member and the second member so that the first and second members are wedge-shaped.

8. The method according to claim 1 wherein the method further comprises sending a slurry in a fermentation tank back to the first member and treating the slurry with ultrasound from transducers.

9. The method according to claim 8 wherein the method further comprises ultrasound treating the slurry prior to sending the slurry to a press unit.

10. A method of treating a medium with an ultrasonic energy comprising:

providing a first movable endless member for treatment of a medium, and a first ultrasonic transducer disposed a first distance from the first member, a second movable endless member disposed opposite to the first member and a second ultrasonic transducer disposed at a second distance from the second member;

moving the first and second members;

feeding the medium between the first and second members; and the transducers generating pressure pulses through the first and second members to form imploding bubbles in the medium disposed between the members, the bubbles having a critical diameter prior to implosion that is greater than the first distance and the second distance to prevent the bubbles from being captured between the first and second distances.

* * * * *